Aug. 4, 1953 R. V. LINDQUIST Plant Pat. 1,209
ROSE PLANT
Filed July 18, 1952
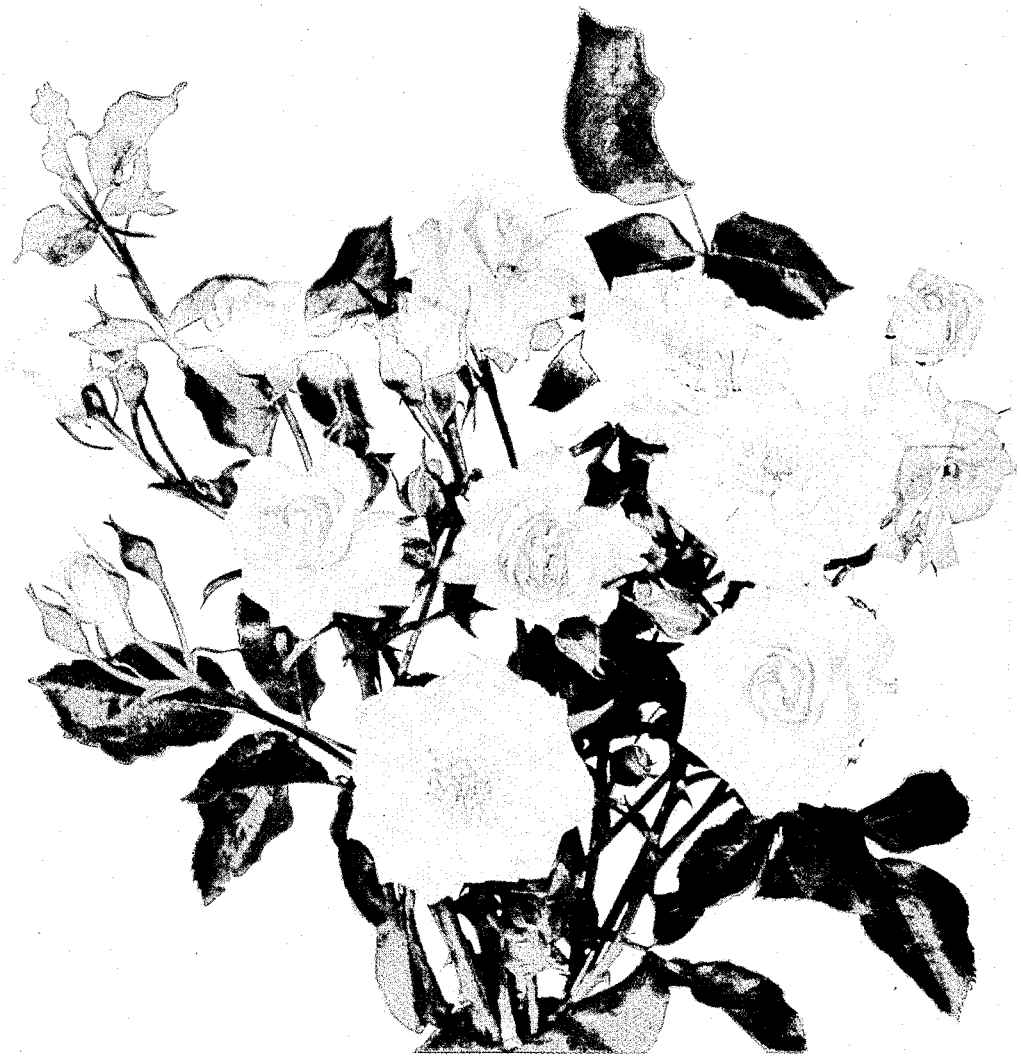
Inventor.
R. V. Lindquist
By: Robb & Robb
Attorneys.

Patented Aug. 4, 1953

Plant Pat. 1,209

UNITED STATES PATENT OFFICE 1,209

ROSE PLANT

Robert V. Lindquist, Hemet, Calif., assignor to Hemet Wholesale Nursery, Hemet, Calif., a partnership Application July 18, 1952, Serial No. 299,781

1 Claim. (Cl. 47—61)

The present invention relates to a new and distinct variety of rose plant of the hybrid polyantha class, originated by me by crossing the variety "Floradora" (unpatented) with the variety "Pinocchio" (Plant Patent No. 484).

As the result of this breeding, I have produced a new variety of rose that is particularly distinctive by reason of its unique combination of general characteristics such as the attractive color of the blooms, freedom of bloom, attractive foliage and superior habits of growth.

More particularly speaking, my new variety is primarily distinguished from its parents, as well as from all other varieties of its class, by the following combination of outstanding features:

(1) The blooms have a moderate to strong, spicy fragrance which is entirely different from that of either parent, and which does not normally occur in polyantha varieties;

(2) In the bud stage, the blooms are high-centered, symmetrical and extremely well-formed, and the substantially perfect formation is maintained from the bud stage through the stage of fully open blooms;

(3) The aforementioned well-formed buds and open flowers are still further enhanced by the attractive and beautiful color shades thereof, the color of the flowers running from Rose Pink to Neyron Rose in general color tonality, shading into Rose Opal as the flower ages, these colors being especially distinctive and unique in a rose of this class;

(4) In its habits of growth, the plants are compact, bushy, well-formed and heavily clothed with fine, glossy, leathery and disease-resistant foliage, said foliage being particularly resistant to blackspot and mildew, and the foliage being winter-hardy and maintaining its attractiveness when subjected to cold Fall weather conditions.

Asexual reproduction of my new variety by budding at Hemet, California, shows that the foregoing characteristics and distinctions come true to form and are established and transmitted through succeeding propagations.

The accompanying drawing shows typical specimens of my new rose variety with the flowers and foliage in different stages of development, and with the colors depicted as nearly true as it is reasonably possible to make the same in an illustration of this character.

The following is a detailed description of my new variety, with color terminology in accordance with Robert F. Wilson's Horticultural Colour Chart, except where general terms of ordinary dictionary significance are obvious:

Type: Hardy; semi-dwarf (approximately attaining the height of its parent "Pinocchio"); bush; outdoor; seedling; for garden decoration.

Class: Hybrid polyantha.

Breeding: Seedling.

*Seed parent.*—"Floradora."

*Pollen parent.*—"Pinocchio."

Propagation: Holds its distinguishing characteristics through succeeding propagations by budding.

*Flower*

Locality where grown and observed: Hemet, California.

Continuity: Continuous.

Fragrance: Moderate to strong; spicy.

Flowers borne: Occasionally singly; often 2 to 3, but usually several to stem; in regular, rounded pyramidal cluster; on normal strength, medium length stems.

Quantity of bloom: Free, outdoors.

Bud:

*Peduncle.*—Short; medium weight; erect; stiff; medium green while small, but becoming reddish-bronze or almost bronze when exposed to sunlight; entirely smooth, but with a few reddish-brown glandular hairs.

*Before calyx breaks.*—Size—small; total of 5 sepals, with 3 alternate sepals having 1 to 3 short (⅛" to ¼"), but narrow ($\frac{1}{32}$") lateral appendages. Form—short; ovoid, with small appendages on the surface of the bud; with slender, much-cut foliaceous parts extending beyond the tip of the bud equal to one-fourth of its length. Color—Empire Rose, Plate 0621.

*As calyx breaks.*—Color—Neyron Rose, Plate 623/1, shading to Porcelain Rose, Plate 620/1, towards base and Sap Green, Plate 62/3, at base of petals, and usually bordered with Rose Opal, Plate 022 to 022/1, at upper margin and midriff of petals.

*As first petal opens.*—Size—medium. Form—short; ovoid. Color: outside—Rose Pink, Plate 427/2, shading to Neyron Rose, Plate 623/2, and Phlox Pink, Plate 625/2, at margin; inside—Rose Pink, Plate 427/2, with Neyron Rose, Plate 623/2, veins.

*Opening.*—Opens up well, but is retarded by cold weather and greatly accelerated by hot weather.

Bloom:

*Size, when fully open.*—Medium; 2½ inches to 3½ inches.

*Petalage.*—Semi-double; from 12 to 35, but usually from 25 to 35 petals arranged regularly averaging 28 petals in the month of May, with 6 to 10 petaloids, singling out to less petalage in hot weather.

*Form.*—Very high-centered at first, but becoming open-cupped; petals being at first very tightly rolled inward, but becoming later, at maturity, very loosely rolled outward.

Petals: Thin, with both inside and outside satiny.

*Shape.*—Outside—round, with short apex. Intermediate—round, with short apex. Inside—oval, with irregular notches.

This description of a newly opened flower was made from a rose grown outdoors in the month of May, at Hemet, California:

*Color.*—Outside petal: outside surface—Rose Pink, Plate 427/2, shading to Plate 427/1, and even to Plate 427, at upper margin, and to Plate 427/3 near base; inside surface—Rose Pink, Plate 427/2, shading to Plate 427/1, at upper margin, and to Plate 427/3 at base, finally becoming Uranium Green, Plate 63/3, at actual base of petals; outside petals occasionally tipped with Rose Opal, Plate 022 to 022/1. Intermediate petal: outside surface—Neyron Rose, Plate 623/2, at center, to Plate 623/1, near petal margin; inside surface—Porcelain Rose, Plate 620/2, to Neyron Rose, Plate 623/2, near petal margin. Inner petal: outside surface—Porcelain Rose, Plate 620/1, near center to Neyron Rose, plate 623/1, near margin; inside surface—Porcelain Rose, Plate 620/1, near center, to Neyron Rose, Plate 623/1, near margin.

This description was made from a rose that was open for three days outdoors in the month of May, at Hemet, California:

*Color.*—Outside petal: outside surface—from Rose Pink, Plate 427/3, at base of petal, to Plate 427/2 and Plate 427/1, at center edges of petals; occasionally Rose Opal, Plate 022/2, tinged to Uranium Green, Plate 63/3, at extreme base of petals; inside surface—from Rose Pink, Plate 427/3, at base of petal, to Plate 427/2 and Plate 427/1, at center edges of petals; occasionally Rose Opal, Plate 022/2, tinged to Uranium Green, Plate 63/3, at extreme base of petals. Inside petal: outside surface—from Rose Pink, Plate 427/3, at base of petal, to Plate 427/2 and Plate 427/1, at center edges of petals; occasionally Rose Opal, Plate 022/2, tinged to Uranium Green, Plate 63/3, at extreme base of petals; inside surface—from Rose Pink, Plate 427/3, at base of petal, to Plate 427/2 and Plate 427/1, at center edges of petals, with large areas of Rose Opal, Plate 022/1 and Plate 022/2; occasionally Rose Opal, Plate 022/2 tinged to Uranium Green, Plate 63/3, at extreme base of petals.

*General color effect.*—Newly opened flower—Rose Pink, Plate 427/2, to Neyron Rose, Plate 623/2. Three days open—Rose Pink, Plate 427/2, to Neyron Rose, Plate 623/2, heavily tinged with Rose Opal, Plate 022/2.

*Behavior.*—Drop off cleanly; color fades to

Rose Pink, Plate 427/3, at margin in dry weather.

*Flower longevity.*—On bush in garden—3 days in month of May. Cut roses grown outdoors and kept at living-room temperatures—3 to 4 days in month of May.

*Reproductive organs*

Stamens: Many; arranged irregularly about pistils; only occasional petaloids outside anthers.

Filaments: Medium length; most with anthers. Color—varying from Crimson, Plate 22/1, on newly opened flowers, to Azalea Pink, Plate 618/3, in fully open flowers.

Anthers: Medium size; all open at once. Color—Orange Buff, Plate 507.

Pollen: Very abundant. Color—yellow.

Pistils: Many.

Styles: Even; short; very thin; bunched tightly.

Stigma: Color—Primrose Yellow, Plate 601/3.

Ovaries: All enclosed in calyx.

Hips: Globular; very smooth; walls thin. Color—orange to russet.

Sepals: Falling soon; very short; curled. Color; inner surface—Lavender Green, Plate 000761/2, often tinged with anthocyanin pigment; outer surface—Scheele's Green, Plate 860/3, often tinged with anthocyanin pigment.

Seeds: Many; medium size.

*Plant*

Foliage:

*Leaves.*—Compound of 3 to 7, but usually 5, leaflets; normal abundance; medium size; heavy; leathery; glossy.

*Leaflets.*—Shape—oval, with apex acute; base round; margin simply serrate.

*Color.*—Mature: upper surface—dark green; under surface—normal green. Young: upper surface — green-bronze, heavily tinged with anthocyanin pigment; under surface—normal green, lightly tinged with anthocyanin pigment.

*Rachis.*—Medium caliper. Upper side—grooved, with glandular hairs. Under side—smooth; often prickly, with 2 to 3 prickles.

*Stipules.*—Medium length; narrow; with medium length points turning out at an angle of about 45°.

*Disease.*—Resistant to mildew and blackspot, as determined by comparison with other hybrid polyanthas grown under comparable conditions.

Growth:

*Habit.*—Semi-dwarf; bushy; upright; much-branched.

*Growth.*—Moderately vigorous.

*Canes.*—Medium caliper.

*Main stems.*—Color—Bright green-bronze; around May 1st, those main stems which were pruned back in previous December, tend to green color, while new heavy canes are heavily tinged with anthocyanin pigment when exposed to sunlight; on maturing, the stems tend to turn green as more foliage develops. Thorns—several to many; medium length; hooked downward; with long, narrow base. Prickles—none. Hairs—few.

*Branches.*—Color—bright green or slightly bronzed. Thorns—several; short to medium length; hooked downward; with long, narrow base. Prickles—none. Hairs—few.

*New shoots.*—Color—bright green, but heavily bronzed. Thorns—several to many; medium length; hooked downward; with long, narrow base. Prickles—none. Hairs—few; very few hairs toward ends of branches, and visible only against direct sunlight.

I claim:

A new and distinct variety of rose plant of the hybrid polyantha class, substantially as herein shown and described, characterized particularly as to novelty by its compact, bushy, well-formed and free-blooming habits of growth, by its abundance of glossy, leathery, winter-hardy and disease-resistant foliage, by the well-formed, symmetrical and high-centered form of its blooms from the bud stage through the full-open stage, by the Rose Pink to Neyron Rose general color tonality of its blooms, shading to Rose Opal as the blooms age, and by the relatively strong and spicy fragrance of its blooms.

ROBERT V. LINDQUIST.

No references cited.